(12) United States Patent
Wisniewski

(10) Patent No.: US 6,858,424 B2
(45) Date of Patent: Feb. 22, 2005

(54) CRYOPRESERVATION VIAL APPARATUS AND METHODS

(75) Inventor: Richard Wisniewski, San Mateo, CA (US)

(73) Assignee: Integrated Biosystems, Inc., Napa, CA (US)

( * ) Notice: Subject to any disclaimer, the term of this patent is extended or adjusted under 35 U.S.C. 154(b) by 467 days.

(21) Appl. No.: 09/991,335

(22) Filed: Nov. 13, 2001

(65) Prior Publication Data

US 2002/0110907 A1 Aug. 15, 2002

Related U.S. Application Data

(63) Continuation of application No. 09/483,191, filed on Jan. 14, 2000, now Pat. No. 6,337,205, which is a continuation-in-part of application No. 09/003,283, filed on Jan. 6, 1998, now Pat. No. 6,079,215.

(51) Int. Cl.⁷ .............................. C12M 1/02; C12N 1/04
(52) U.S. Cl. ..................... 435/307.1; 435/1.3; 435/260; 220/560.04; 62/78; 62/457.9
(58) Field of Search ........................... 735/1, 3, 2, 260, 735/283.1, 307.1; 165/61; 422/102; 270/560.04, 560.09; 62/78, 457.9

(56) References Cited

U.S. PATENT DOCUMENTS

| | | | |
|---|---|---|---|
| 2,879,005 A | 3/1959 | Jarvis | 241/14 |
| 3,214,928 A | 11/1965 | Oberdorfer | 62/63 |
| 4,314,451 A | 2/1982 | Leeds et al. | 62/68 |
| 4,476,686 A | 10/1984 | Madsen et al. | 62/63 |
| 4,490,982 A | 1/1985 | Christmas | |
| 4,687,672 A | 8/1987 | Vitkovsky | 426/524 |
| 4,761,962 A | 8/1988 | Andersson | 62/68 |
| 4,799,358 A | 1/1989 | Knopf et al. | |
| 4,843,840 A | 7/1989 | Gibson | 62/375 |
| 4,967,564 A | 11/1990 | Strasser | 62/47 |
| 5,059,399 A | 10/1991 | Schilling | 422/102 |
| 5,205,129 A | 4/1993 | Wright et al. | 62/68 |
| 5,689,961 A | 11/1997 | Cosman | |
| 5,728,417 A | 3/1998 | Horn et al. | 426/231 |
| 5,732,559 A | 3/1998 | Horn et al. | 62/62 |
| 5,743,097 A | 4/1998 | Frank | 62/68 |
| 5,964,100 A | 10/1999 | Wisniewski | 62/373 |
| 6,065,294 A | 5/2000 | Hammerstedt et al. | 62/3.3 |
| 6,079,215 A | 6/2000 | Wisniewski | 62/46.1 |
| 6,196,296 B1 | 3/2001 | Wisniewski et al. | 165/47 |

FOREIGN PATENT DOCUMENTS

| | | | |
|---|---|---|---|
| CA | 2 041 341 | 10/1992 | .......... F25D/31/00 |
| DE | 38 33 753 A1 | 8/1989 | .......... F25D/31/00 |
| EP | 0 560 509 A1 | 9/1993 | ............ A23P/1/08 |
| EP | 0642828 | 3/1995 | .......... B01L/33/00 |
| JP | 7-294085 | 11/1995 | |
| WO | WO 98 34078 A | 8/1998 | |

OTHER PUBLICATIONS

Japanese Patent JP 07 294085 (Iwatani Ind. Co., Ltd.), Nov. 10, 1995 (Abstract), Database WPI, Section PQ, Week 9603, Derwent Publications Ltd., London. [Note: Same as Japanese No. 7–294085.].

*Primary Examiner*—William H. Beisner
(74) *Attorney, Agent, or Firm*—Heslin Rothenberg Farley & Mesiti P.C.

(57) ABSTRACT

Disclosed is a biopharmaceutical product cryopreservation system, for cryopreserving a biopharmaceutical product that includes a cryopreservation compartment; a cryopreservation fluid located within the cryopreservation compartment; and a biopharmaceutical product cryopreservation vial located within the cryopreservation compartment and surrounded by the cryopreservation fluid, and the biopharmaceutical product cryopreservation vial including a body that includes an oblong cross-section defining proximal and distal ends of the body, and at least one nucleating structure, coupled to a distal end of the body, and the body including a cryogenically stable material that is compatible with biopharmaceutical products. Also disclosed are cryopreservation vials and methods of cryopreserving biopharmaceutical products.

54 Claims, 10 Drawing Sheets

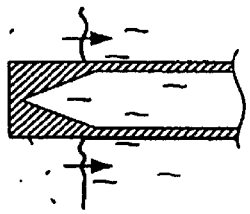
FIG.4O
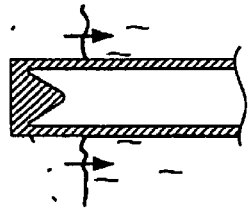
FIG.4P
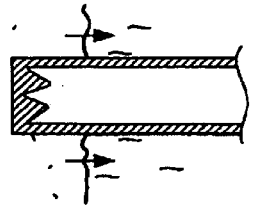
FIG.4Q
FIG.4R
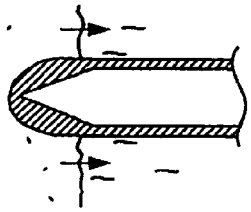
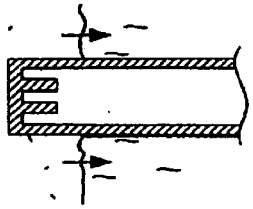
FIG.4S
FIG.4T
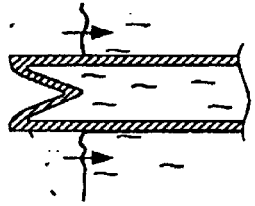
FIG.4V
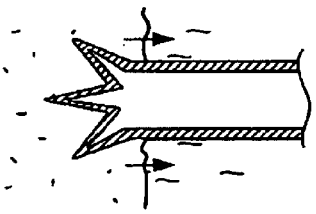
FIG.4W
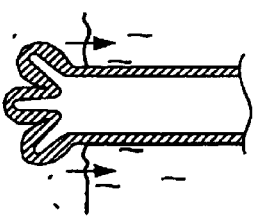
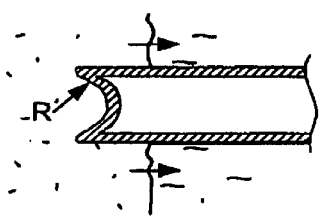
FIG.4U
FIG.4X
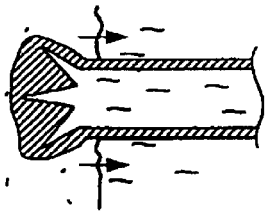

US 6,858,424 B2

CRYOPRESERVATION VIAL APPARATUS AND METHODS

REFERENCE TO RELATED APPLICATIONS

This application is a continuation of U.S. patent application Ser. No. 09/483,191 filed Jan. 14, 2000, now U.S. Pat. No. 6,337,205; which is a continuation-in-part of U.S. patent application Ser. No. 09/003,283 filed Jan. 6, 1998, now U.S. Pat. No. 6,079,215.

BACKGROUND OF THE INVENTION

1. Field of the Invention

This invention relates to biopharmaceutical product cryogenic preservation methods and apparatus, more particularly this invention relates to biopharmaceutical product cryogenic preservation using a cryopreservation vial apparatus and methods.

2. Description of Related Art

Cryopreservation and cryoprocessing of biopharmaceutical products is important in the manufacturing, use, and sale of these products. However, in order to process many of these products, the cryopreservation or cryoprocessing must be done uniformly and in a controlled manner or the quality and value of the product may be lost. For example, when processing cells for cryopreservation, if the cells are frozen too quickly with too high of a water content, then the cells can develop intracellular ice crystals. As a result, the cells may will rupture and/or become unviable. Another example is the freezing of protein solutions that are formulated for pharmaceutical use. Ideally, freezing of these solutions is uniform throughout the frozen volume. Uniformity of the frozen volume tends to provide, throughout the frozen volume, similar concentrations of solutes similar ice crystal patterns, and similar glassy states of the frozen matrix (uniformity of trapped moisture level, of glass transition temperature, or local glass-ice volumetric ratio, and of glass composition). These characteristics are desirable for achieving uniform product attributes throughout the volume, and reducing product loss. It is desirable to maintain similar freezing conditions independently of the freezing volume. Reproducibility of freezing in large and small samples permits process scale up and testing of small product samples under freezing conditions which may be later encountered in freezing of large volumes of biopharmaceutical products.

Cryopreservation and cryoprocessing is large volumes is especially desirable with respect to biopharmaceutical products. For instance, large scale processing may be useful in manufacturing of biopharmaceutical products. Such large scale processing is described in U.S. Pat. No. 5,964,100; and U.S. patent application Ser. Nos. 08/895,777; 08/895,782; 08/895,936, and 09/003,283. These documents, and all other documents cited to herein, are incorporated by reference as if reproduced fully herein. However, during development of processes for manufacturing the biopharmaceutical products, researchers may not have a lot of the biopharmaceutical product on hand. This makes process development and optimization difficult; there simply may not be enough product available at that stage to fill a vessel of tens or hundreds of liters in volume. Therefore, "scaledown" technologies are needed to simulate large scale, for example production scale, freezing and thawing (i.e. cryopreservation) in very small volumes, for example laboratory scale.

One solution is trying to simulate large scale cryopreservation or cryoprocessing using small volume containers. However, the inventor has uncovered a problem with freezing of small volumes comprising biopharmaceutical products. Under external cooling, a small volume of media comprising a biopharmaceutical product supercools first in a liquid form (reaches thermodynamic inequilibrium) and then rapidly solidifies. The temperature first drops to reach a supercooled state in a liquid (the supercooling occurs in a whole volume of liquid). Then, after the seeding crystals form, the small volume solidifies rapidly taking the heat of solidification. The small volume thus rapidly warms up to the solidification temperature (a short plateau at this level ensues followed by a temperature decline (the solidified small volume is cooled by external cooling).

During rapid solidification of the supercooled small volume, the entire small volume could rapidly solidify with ice crystals rapidly "shooting" into (and through) the solidifying volume. Typically, such crystals shoot from the coldest points on the small volume internal surface. Such rapid crystal growth may be detrimental to the biopharmaceutical product. This is particularly the case if the rapid growth produces very fine crystals, which results in a large biopharmaceutical product-ice interface area, etc. Furthermore, the supercooling effect is more pronounced in smaller volumes than in larger volumes. Therefore, such small volumes may not accurately model cryopreservation and cryoprocessing of larger volumes of biopharmaceuticals.

Accordingly, there is a need for methods and apparatus for cryopreservation and cryoprocessing of biopharmaceutical products that solve the deficiencies noted above.

SUMMARY OF THE INVENTION

In an aspect, the invention relates to a biopharmaceutical product cryopreservation system, for cryopreserving a biopharmaceutical product, comprising a cryopreservation compartment; a cryopreservation fluid located within the cryopreservation compartment; and a biopharmaceutical product cryopreservation vial located within the cryopreservation compartment and surrounded by the cryopreservation fluid, and the biopharmaceutical product cryopreservation vial comprising a body that comprises an oblong cross-section defining proximal and distal ends of the body, and at least one nucleating structure, coupled to a distal end of the body, and the body comprising a cryogenically stable material that is compatible with biopharmaceutical products.

In another aspect, the invention relates to a method of cryopreserving biopharmaceutical products comprising providing a cryopreservation compartment; locating a biopharmaceutical product cryopreservation vial within the cryopreservation compartment, wherein the biopharmaceutical product cryopreservation vial comprises a body that comprises an oblong cross-section defining proximal and distal ends of the body, and at least one nucleating structure, coupled to a distal end of the body, and the body comprising a cryogenically stable material that is compatible with biopharmaceutical products locating a cryopreservation fluid in a space outside of the cryopreservation vial but within the cryopreservation compartment; and removing heat from the cryopreservation compartment, thereby freezing the cryopreservation fluid.

In still another aspect, the invention relates to a biopharmaceutical product cryopreservation vial comprising a body that comprises an oblong cross-section defining proximal and distal ends of the body, at least one nucleating structure, coupled to a distal end of the body, and the body comprising a cryogenically stable material that is compatible with biopharmaceutical products.

DETAILED DESCRIPTION OF THE INVENTION

The inventor has unexpectedly discovered that the problems in the art noted above may be solved using a biopharmaceutical product cryopreservation vial comprising a body comprising a cryogenically stable material that is compatible with biopharmaceutical products, wherein the body comprises an oblong cross-section, and ice crystal-nucleating structures located at opposite ends of the oblong cross-section.

Figure 1:
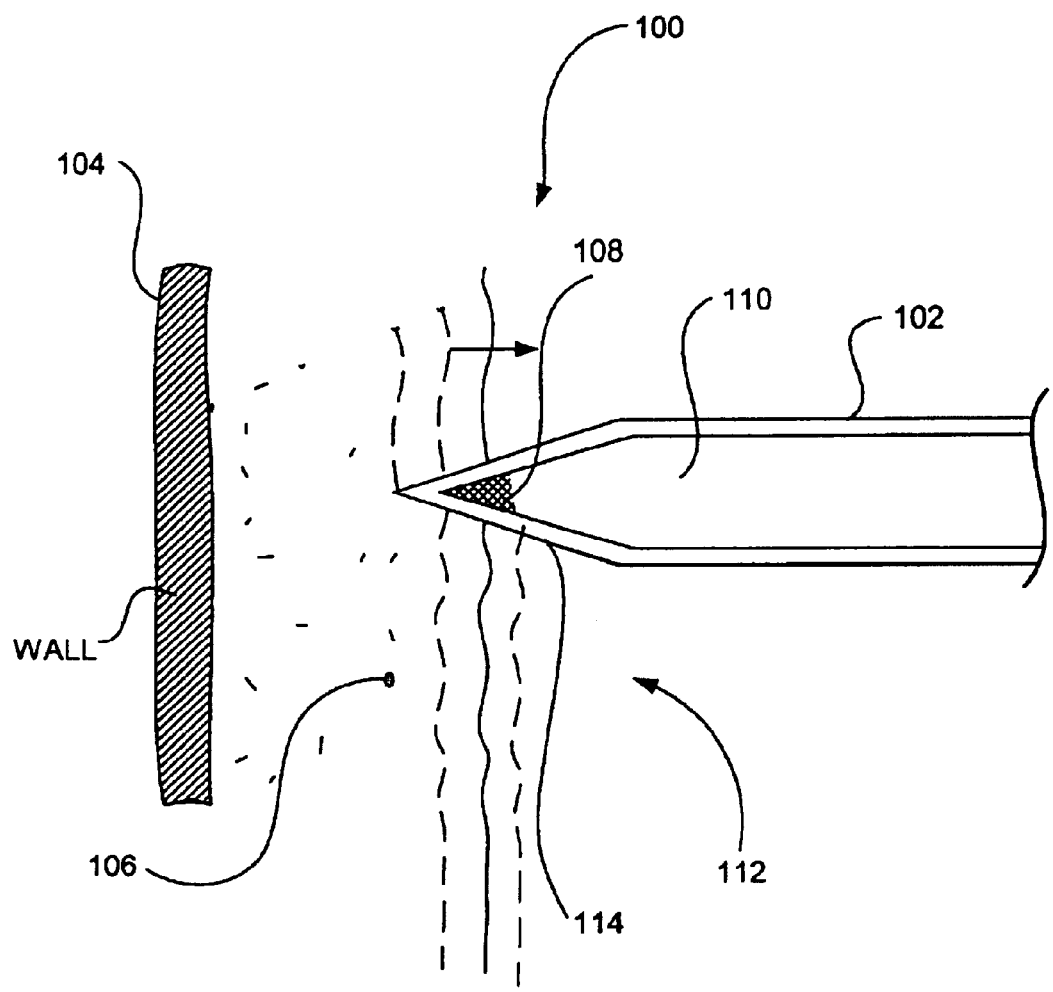
FIG. 1 shows a cross sectional view of a cryopreservation system according to the invention.
Figure 2A:
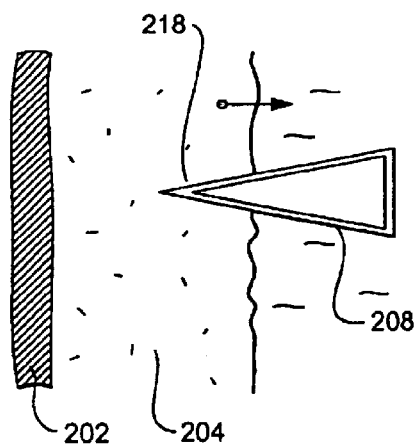
FIGS. 2A–D show a cross sectional view of cryopreservation vials according to the invention.
Figure 2B:
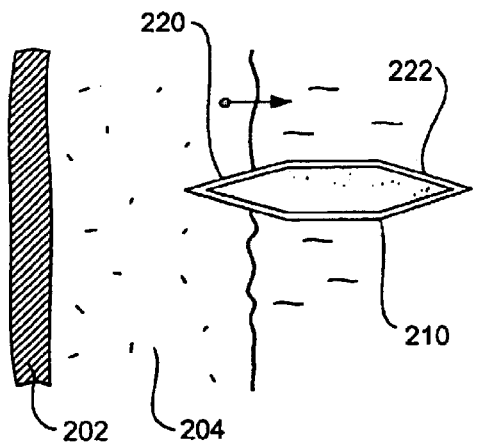
Figure 2C:
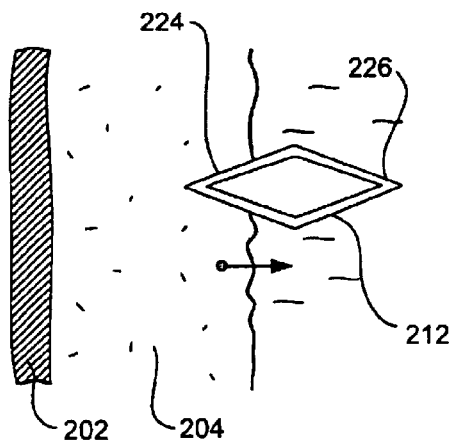
Figure 2D:
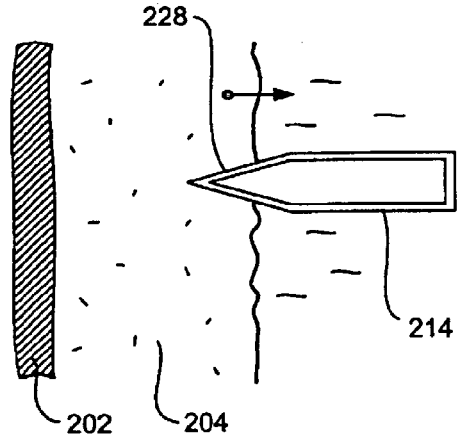

Typically, as shown in FIG. 1, inventive biopharmaceutical product cryopreservation vial 102 is placed within the inventive biopharmaceutical product cryopreservation system 100. During operation, a freezing front 106 in cryopreservation compartment 112, the freezing front 106 being defined by freezing of the cryopreservation fluid within cryopreservation compartment 112, approaches a nucleating end structure 114 of cryopreservation vial 102. As freezing front 106 progresses, the nucleating structure 114 wall temperature drops below 0 C., e.g. below the aqueous solution solidification temperature. This is because there is a temperature gradient in the solid front (decreasing temperature from the liquid-solid interface towards cooled wall 104 of the cryopreservation compartment). As a consequence, nucleating 114 structure is shallowly embedded in solid front 106.

The oblong cross-section of the cryopreservation vial body reduces or avoids supercooling of media in the cryopreservation vial when a long axis of the oblong cross-section is oriented at an angle to the solid front. Such an orientation tends to insure that the heat transfer surface area between the vial and the liquid cryopreservation fluid (this liquid phase stays near 0 C.), is larger during the initial freezing process than the heat transfer surface area between the vial and the frozen cryopreservation fluid. As a result the media comprising the biopharmaceutical product remains at near 0 C. (e.g. the temperature of the outer liquid phase) and only drops near the nucleating structure (this wall is cooled by the embedding outside solid front). This local temperature drop zone occupies a zone 108 of the cryopreservation vial internal product volume.

While not wishing to be bound by a particular mechanism of action, as such knowledge may not be necessary to practice the invention, it appears that ice crystal formation inside the cryopreservation vial is enhanced through the presence of a nucleating structure that permits formation of relatively immobile clusters of media molecules, preferably water molecules, on a macroscopic scale. This may be accomplished by utilizing a nucleating structure to immobilize the boundary layer of liquid biopharmaceutical product near the interior cryopreservation vial walls, thus reducing or eliminating convectional effects. Additionally, the nucleating structure acts to lower the local temperature of the relatively immobile clusters of media molecules clusters.

FIG. 1 further illustrates how the inventive nucleating structure may accomplish these goals.

A temperature gradient forms in zone 108 (in the liquid phase) leading to localized supercooling within or near nucleating structure 114. The amount of bulk biopharmaceutical product affected by supercooling in the overall cryopreservation vial volume is significantly reduced compared to containers lacking a nucleating structure; preferably the amount of bulk product so affected is substantially limited to the pharmaceutical product located in and around the nucleating structure. In fact, bulk temperature readings inside the cryopreservation vial do not evidence any supercooling effects. As a consequence, the liquid temperature in the cryopreservation vial stays near 0 Deg. C., similar to the temperature of the surrounding cryopreservation fluid contained within the cryopreservation compartment.

The temperature gradient promotes formation of ice crystals on the cold wall and their growth in a form of dendrites. The dendritic front forms inside the cryopreservation vial and its position equalizes with the position of the solidification front outside the cryopreservation vial. Both fronts then move together along the cryopreservation vial until the cryopreservation vial end is reached (all product inside the vial becomes solidified). The cryopreservation vial can be placed in between two approaching solid fronts and then freezing in the cryopreservation vial occurs from more than one nucleating structure and ensues towards a central point of the cryopreservation vial. Solidification fronts may meet in central points outside and inside of the cassette. In such a way the inventive cryopreservation system may model freezing in a large liquid volume using very little product.

A variety of different cross-sectional geometries are suitable for the cryopreservation vial according to the invention. FIGS. 2A–D show various embodiments of cryopreservation vials according to the invention, including cryopreservation compartment wall 202; freezing front 204; and cryopreservation vials 208, 210, 212, and 214 that comprise nucleating structures 218, 220, 222, 224, 226, and 228. In these embodiments, each of cryopreservation vials 208, 210, 212, and 214 are embedded in freezing front 204, which is being generated by the cooling effects of cryopreservation compartment wall 202. Nucleating structures 218, 220, 222, 224, 226, and 228 serve to initiate the localized supercooling according to the invention.

Figure 3A:
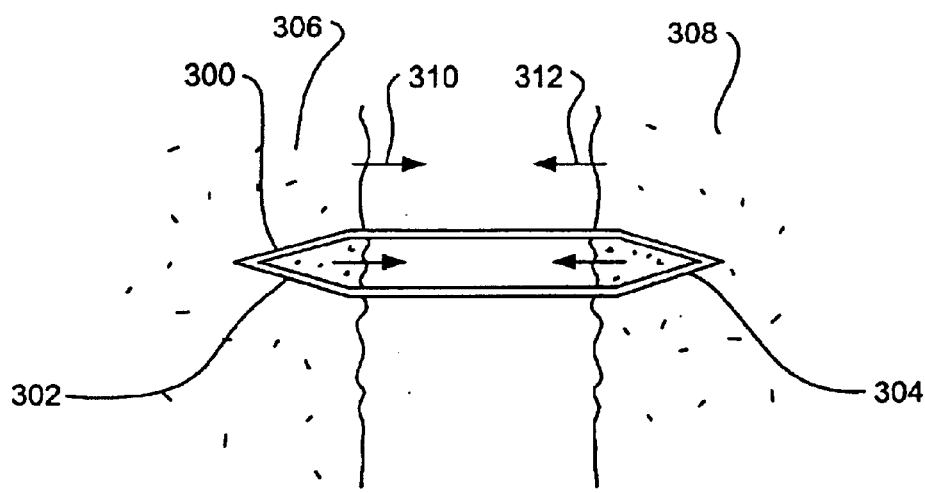
FIGS. 3A–C show cross sectional views and an elevation of cryopreservation vials according to the invention.
Figure 3B:
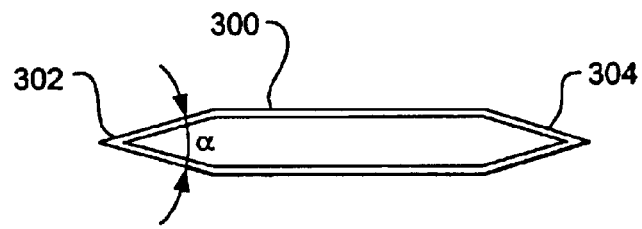
Figure 3C:
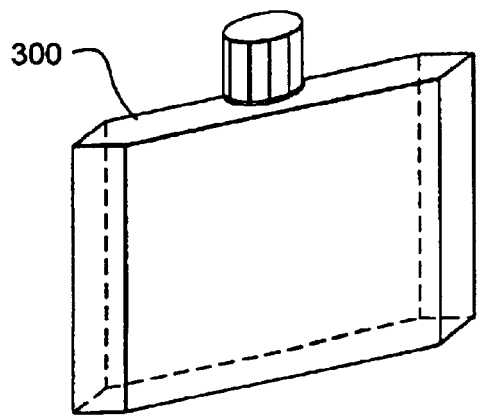

Cryopreservation vials having cross-sectional geometries comprising more than one nucleating structure may be useful in the practice of this embodiment. Multiple nucleating structures, or multiple points where vials walls are in local proximity, may be used to speed the freezing process within the cryopreservation vial. In a preferable embodiment, the number of nucleating structures present on a cryopreservation vial according to the invention may range from one to about one hundred, more preferably from about two to about ten. For example, those geometries shown in FIGS. 2A–D may be used. An illustration of this is shown in FIG. 3A. Cryopreservation vial 300 has a similar cross-section to cryopreservation vial 210, with nucleating structures 302 and 304 being embedded in freezing fronts 306 and 308 that are advancing in the directions given by arrows 310 and 312. As shown in FIG. 3B, the length of the particular embodiment illustrated by cryopreservation vial 300 is generally greater than the width. Further, the interior angle alpha, which is the angle formed by nucleating structure 302, is preferably less than about 90 degrees. FIG. 3C shows an isometric elevation of cryopreservation vial 300, having the cross-section illustrated in FIGS. 3A–B.

The body of which the inventive cryopreservation vial is comprised should be oblong, e.g. the lengths of the body axes should significantly differ, thus defining a proximal and distal end. The distal end is distal from a center point of the cryopreservation vial (for example the ends of an oval or the points of a "star"). The oblong shape of the body produces a large wall surface area versus the cryopreservation vial interior volume. This surface area is utilized for heat transfer that maintains the inside liquid temperature steady and close to outside liquid temperature (no supercooling of the inside liquid). The ratio of lengths of the axis is preferably within the range of about 1.3:1 to about 450:1, more preferably from about 8:1 to about 26:1. The distances between the interior walls along the longer axis preferably ranges from about 0.1 mm to about 500 mm, more preferably about 5 mm to about 35 mm. The ratio of lengths of the nucleating structure to the cryopreservation vial long axis preferably range from about 1:1 (for example, a triangular shape of vial) through about 1:2 (for example, a diamond shape) to about 1:500,000 (for example, fine corrugations at the vial end wall). A more preferable range of this ratio is from about 1:2 to about 1:800.

The nucleating structures according to the invention may have a variety of shapes. In general, the inventive nucleating structures are coupled to a distal end of the body. For example, nucleating structures may be configured in a convex extension from the body, which can be preferably oriented to face an incoming solid front. The extensions may have a variety of shapes. For example, the nucleating structures may be in the shape of single or multiple narrow grooves, preferably with convex corners. These corners may have various angles, preferably from about 0.01 Deg to about 90 Deg, more preferably from about five to about forty Deg. In a preferable embodiment, a principle of nucleating structure design is to create a point of local proximity (up to and including a point of contact, wherein the two surfaces that are meeting describe a substantially acute angle at the point of contact), where there is still some media that can be locally supercooled without inducing supercooling of the bulk volume of media in the cryopreservation vial.

In certain embodiments, the nucleating structures may be configured so as position the interior walls of the nucleating structures to be in local proximity in the tip cavity. In a preferable embodiment, the nucleating structure comprises one or more points of local proximity, more preferably two or more points of local proximity. Such areas of local proximity may become a source of ice nuclei with relatively very small local supercooling in the surrounding liquid, while the rest of the media is not supercooled, e.g. supercooling may occur only in the nucleating structure of the cryopreservation vial; more precisely supercooling may be concentrated near the point of local proximity. The points of local proximity may be created by forming the vial wall internal sides into extensions (nipples) located opposite to each other, preferably with their internal surface tips spaced apart from about 0.001 mm to about 5.0 mm, more preferably from about 0.04 mm to about 0.5 mm. In a preferable embodiment, the walls may be spaced so closely that, given any flexing of the cryopreservation vial walls during the embedding of the nucleating structure into the solid front, the walls in local proximity are moved into actual contact each other.

Heat conduction through the walls will cause these nipples to be cold spots and the proximity of their tips would cause formation of locally supercooled microscopic zone between the tips. This zone becomes a nucleation site for the first ice crystals. On formation of these first ice crystals, the nucleating structure fills with ice crystals which continue growing and follow the temperature gradient formed between a distal portion of the body and the rest of the vial volume. The ice crystals form a dendritic crystal front which moves together with the dendritic crystal front outside the cryopreservation vial (vial is being embedded by externally solidifying material).

Figure 4A:
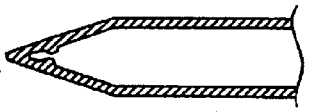
FIGS. 4A–V show cross sectional views of nucleating structures according to the invention.
Figure 4B:
Figure 4C:
Figure 4D:
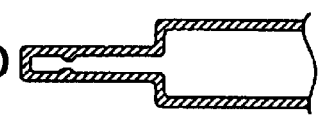
Figure 4E:
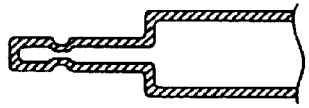
Figure 4F:
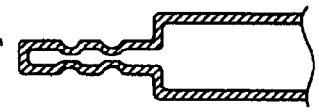
Figure 4G:
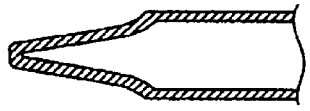
Figure 4H:
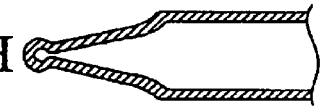
Figure 4I:
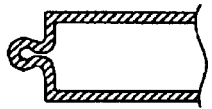
Figure 4J:
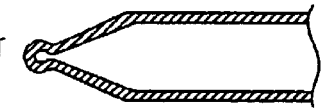
Figure 4K:
Figure 4L:
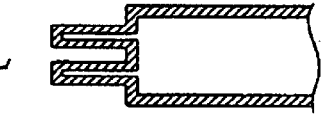
Figure 4M:
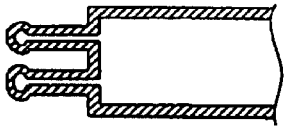
Figure 4N:
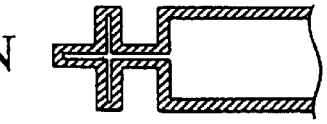

Exemplary geometries for nucleating structures having points of local proximity are shown in FIGS. 4A–V. FIGS. 4A–K, M, and P show inventive nucleating structures singly coupled to distal ends of a body of which a cryopreservation vial is comprised. In FIGS. 4A–K, the nucleating structures possess at least one point of local proximity. In a preferable embodiment, such as that shown in FIG. 4F, the nucleating structure comprises two or more points of local proximity. In various embodiments of the tip detail, the corrugation and nipples may form a single or multiple point contacts, for example, two nipples located near the tip of cartridge end to form the first nucleation zone, as shown in FIGS. 4L–N. Various embodiments of multiple nucleating structures coupled to single bodies are shown in FIGS. 4N–O, and 4Q–V.

There may considerable variety in how the nucleating structures are constructed on the body. For example, the outer surface of the nucleating structure may be extended by corrugations, fins, etc. to increase heat transfer between the nucleating structure and the outside solidifying cryopreservation fluid.

The inventive cryopreservation vial is designed to provide adequate conditions for testing of biopharmaceutical products. It may be sterilized (using steam or other conventional techniques) and during testing can remain sealed (aseptic conditions can be maintained) thus preventing biological product degradation, for example by proteases, or contamination.

The cryogenically stable material is compatible with biopharmaceutical products and has compatibility with the cryopreservation fluid in liquid and frozen state. Important characteristics influencing compatibility of the cryogenically stable material with biopharmaceutical products includes, for example, lack of leaching of biotoxic compounds, minimal biodegradation, minimal surface interactions with product at molecular (example: formation of hydrogen bonds, molecular adsorption), microscopic (example: adsorption binding facilitation due to surface roughness) and macroscopic (example: crevices, accumulating biological material) levels, and chemical resistance (to cleaning agents, solution buffers, etc.). Absence or substantial absence of certain components (such as copper or heavy metals) is preferable to prevent biological molecule denaturation or chelating.

Various polymers can be used as the cryogenically stable material, such as polytetrafluoroethylene, polystyrene, polyethylene or polypropylene. In a preferable embodiment, surface treatments may be applied to a surface of the biopharmaceutical product cryopreservation vial, for example to reduce adsorption of biological molecules or cells (e.g., RF plasma treatment may be applied to the vial surface). Hydrophilic coatings may significantly reduce biopharmaceutical product adsorption and denaturation on the vial surface.

The inventive cryopreservation vial has a wall thickness (other than the nucleating structure, which may have a separate wall thickness) has a lower limit determined by structural strength and vial integrity (e.g. a polymer film that has functionally adequate structural strength and vial integrity). Preferably, this thickness should be at least about 0.001 mm, more preferably at least about 0.05 mm. The maximum vial wall thickness is not necessarily limited; preferably the maximum vial wall thickness may be about 150 mm, more preferably about 30 mm. A ratio of the vial wall thickness to vial internal width can range from about 20:1 to about 1:500,000, preferably from about 5:1 to about 1:50,000. The thickness of the walls of the nucleating structures can be small, equal or larger than the thickness of the remaining vial walls, which are discussed above. If the thermal conductivity of vial material is smaller than the frozen media and/or cryopreservation fluid, then thinner walls of nucleating structures are preferable; likewise when the thermal conductivity of the wall material is larger than the frozen media and/or cryopreservation fluid, then thicker walls can be applied.

In addition to biocompatibility, mechanical strength and chemical resistance the vial material preferably possesses certain properties associated with its application for freezing and thawing processes. Thermal conductivity and/or specific heat of the cryopreservation vial preferably are selected to be substantially similar to those of the frozen media that comprises the biopharmaceutical product and/or the cryopreservation fluid. Often the cryopreservation fluid comprises mostly water such that the frozen cryopreservation fluid has properties similar to ice (ice thermal conductivity is approximately 2.25 [W/m K] at 0 C and 3.94 [W/mK] at −95 C.; ice specific heat is 2.261 and 1.172 [kJ/kg K] respectively).

Preferable specific heats for examples of suitable cryogenically stable materials include (all in [kJ/kg K]) are as follows: polyethylene (at 200 K): 1.11; polypropylene (at 200 K): 1.132; polystyrene (at 300 K): 1.223; polytetrafluoroethylene (at 200 K): 0.6893; Nylon-66 (at 230 K): 1.139. Preferable thermal conductivities for suitable cryogenically stable materials include (all in [W/m K]): Nylon-12: 0.25; Nylon-6 (moldings): 0.24; Nylon-6, 12): 0.22; polycarbonate: 0.20; polyester (cast): 0.17; PEEK: 0.25; PET: 0.15; PVC (rigid): 0.21; Teflon: 0.25. Stainless steel wall material for the vial has thermal conductivity of about 16 [W/m K]. Composites, glasses, ceramics and metals and their alloys can be used as the cryogenically stable material.

In one embodiment of the invention, the thermal conductivity of the vial walls is preferably not substantially higher than those of the biopharmaceutical product and the cryopreservation fluid. If the thermal conductivity of the vial walls is higher then the side walls may act as heat conducting fins causing freezing to occur on the side of the walls well ahead of the freezing fronts in the media and in the cryopreservation fluid. Such a "fin effect" will promote pulling of the inside solid front forward inside the vial. This may make stainless steel and metals less desirable for side walls of the vial in certain applications.

Cryopreservation vial tips, which comprise the nucleating structure and a portion of the cryopreservation vial wall in proximity to the nucleating structure, may be made of the same material as the side walls or can be made with material of higher thermal conductivity (e.g. similar to the frozen product and fluid or higher). If the vial tips possess similar thermal conductivity to the frozen media and cryopreservation fluid, heat flux may flow more smoothly through the vial tips. Such an arrangement promotes freezing of the media comprising the biopharmaceutical product with minimal wall effect, i.e. media freezing at substantially the same rates as the cryopreservation fluid. The vial tips can be made, for example of metals (like stainless steel or titanium) or made of composites or filled polymers (such as epoxy filled with stainless steel powder, epoxy filled with Aluminum powder, or PET filled with graphite fiber).

The use of low thermal conductivity material in the vial tips may create some increased vial wall thermal resistance compared to the frozen cryopreservation fluid, thus impacting the solid front growth inside the cryopreservation vial. The vial tip configuration not only facilitates ice crystal nucleation but also may focus heat flux on the vial end wall from the outer freezing fluid to balance for lower thermal conductivity of the vial wall. Further, the tips may be configured to deflect the heat flux from a cooling surfaces, if desired. In this manner, the vial tip configuration may be adjusted to partially or substantially compensate for differences in thermal conductivity between the cryopreservation fluid, the cryopreservation vial wall, the cryopreservation vial tips, the nucleating structures, and the media comprising the biopharmaceutical product.

Figure 5A:
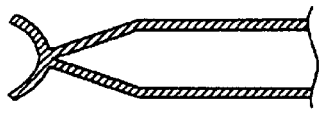
FIGS. 5A–I show cross sectional views of vial focusing tips according to the invention.
Figure 5B:
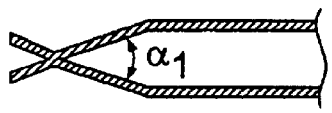
Figure 5C:
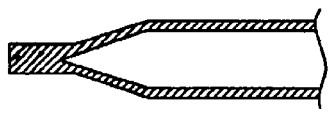
Figure 5D:
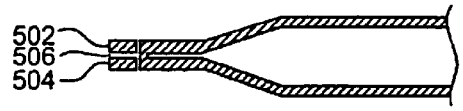
Figure 5E:
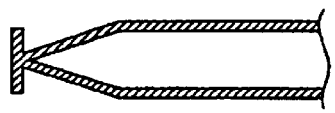
Figure 5F:
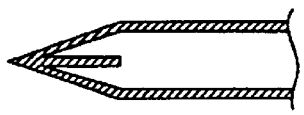
Figure 5G:
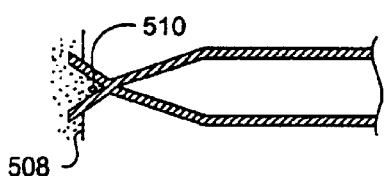
Figure 5H:
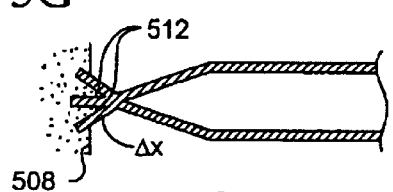
Figure 5I:
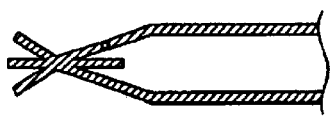
Figure 6A:
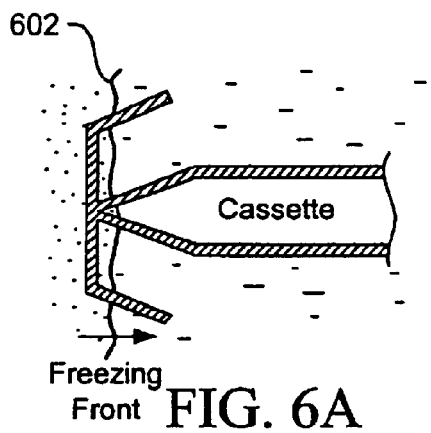
FIGS. 6A–E show cross sectional view of vial deflecting tips according to the invention.
Figure 6B:
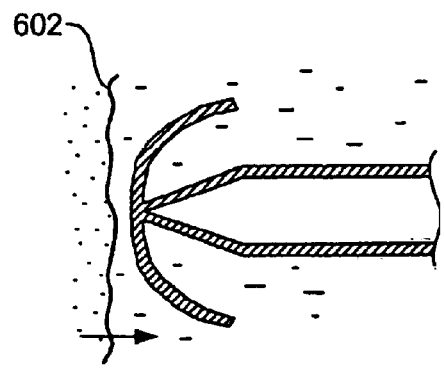
Figure 6C:
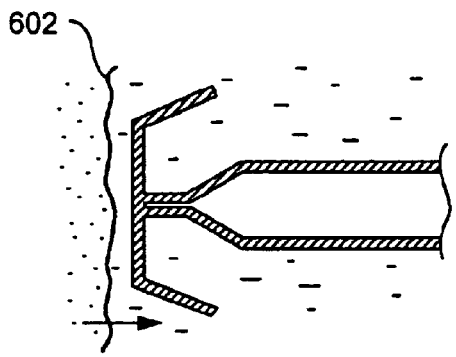
Figure 6D:
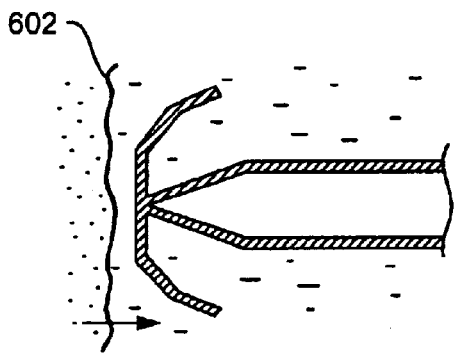
Figure 6E:
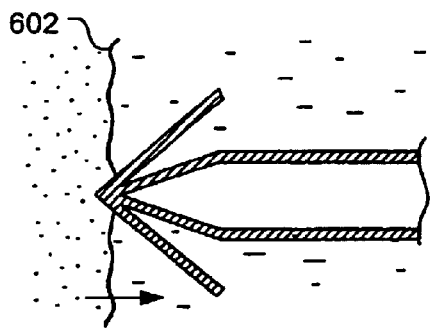

Examples of vial focusing tips, which serve to focus the heat flux (preferably on the nucleating structures), are shown in FIGS. 5A–I. FIGS. 5A–B shows vial focusing tips comprising external heat transfer fins describing a radius (FIG. 5A) or an angle (FIG. 5B) that are greater than an internal angle formed by the cryopreservation vial inside walls. The difference between the external radius or angle and the internal angle serves to focus the heat flux. FIG. 5C shows a vial focusing tip where a portion of the tip wall has a thermal conductivity greater than or equal to surrounding cryopreservation fluid. This configuration results in heat flux focusing. The embodiment shown in FIG. 5D has a similar structure to the embodiment shown in FIG. 5C, save that a small crevice or space is introduced into the vial tip, wherein the crevice communicates with the internal space of the cryopreservation vial. The heat flux is focused when tip wall thicknesses 502 and 504 are greater than tip thickness 506. FIG. 5E shows another configuration wherein external heat transfer fins are used to focus the heat flux. FIG. 5F shows a configuration wherein internal heat transfer fins are used to focus the heat flux. FIGS. G–H illustrate how external heat transfer fins may serve to focus the heat flux. Oncoming solid front 508 moves at a defined rate. However, between the focusing fins, fronts 510 and 512 move faster than solid front 508, thus focusing the heat flux. FIG. 5I shows how external and internal focusing fins may be combined into a single vial focusing tip.

External fins may be used to deflect heat flux, in addition to their potential focusing role, as discussed above. Examples of vial deflecting tips, which serve to deflect the heat flux, are shown in FIGS. 6A–E. In FIGS. 6A–E, the vial deflecting tips describe external heat transfer fins that face away from oncoming solid front 602 and outwards from the cryopreservation vial. This configuration serves to deflect the heat flux associated with solid front 602 away from the rest of the cryopreservation vial to which the vial deflecting tips is coupled.

Figure 7A:
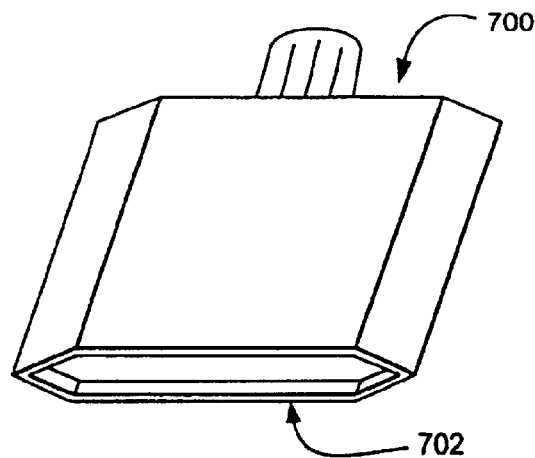
FIGS. 7A–D show and elevation and cross sectional views of cryopreservation vials according to the invention.
Figure 7B:
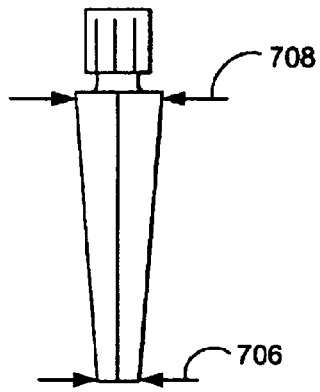
Figure 7C:
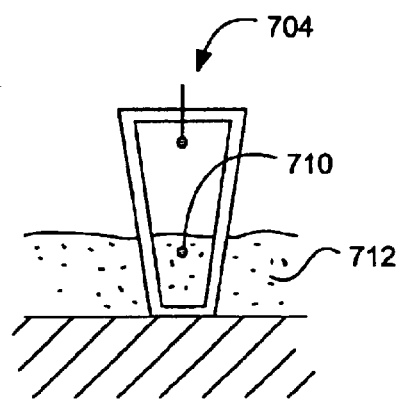
Figure 7D:
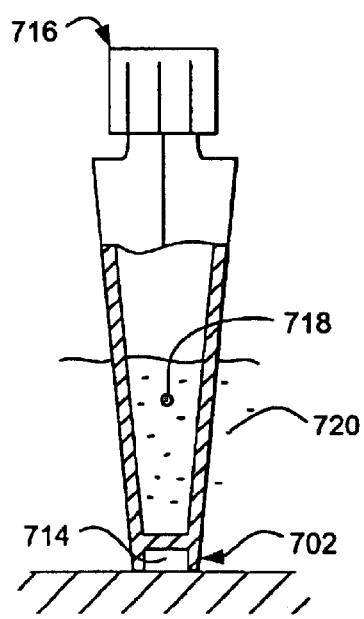

As shown in FIG. 7A, in a preferable embodiment, cryopreservation vial 700 may have a rim 702 around a bottom edge to trap an air pocked when initially submerged in a downward direction into the cryopreservation fluid. This feature tends to reduce heat transfer from the bottom upwards. The air pocket may also facilitate upward cryopreservation vial removal since the bottom is less adherent to the solidified mass below it in the course of the freezing process. FIGS. 7B–C show another preferable embodiment, in which removal of cryopreservation vial 704 from frozen cryopreservation fluid may be facilitated by a tapered shape of the vial—e.g. a cross-sectional widening in the direction of desired removal. This taper can be seen in FIG. 7B which is a side elevation of cryopreservation vial 704, showing bottom cross-sectional distance 706 being shorter than top cross-section distance 708. FIG. 7C shows a cross-section of cryopreservation vial 704, illustrating the tapered shape, and showing the location of media 710 and cryopreservation fluid 712. The cryopreservation vial of FIG. 7D illustrates the combination of the rim embodiment and the tapered shape embodiment in cryopreservation vial 716. Cryopreservation vial 716 contains media 718, and is located in cryopreservation fluid 720. Rim 702 describes an air pocket 714, with the function as described above.

Figure 8A:
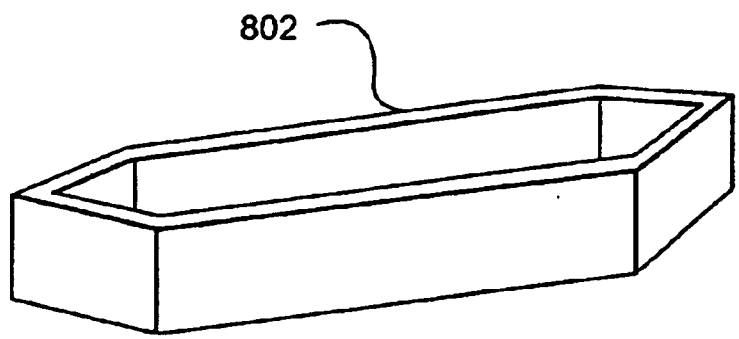
FIGS. 8A–B show a views of a cryopreservation vial nest according to the invention.
Figure 8B:
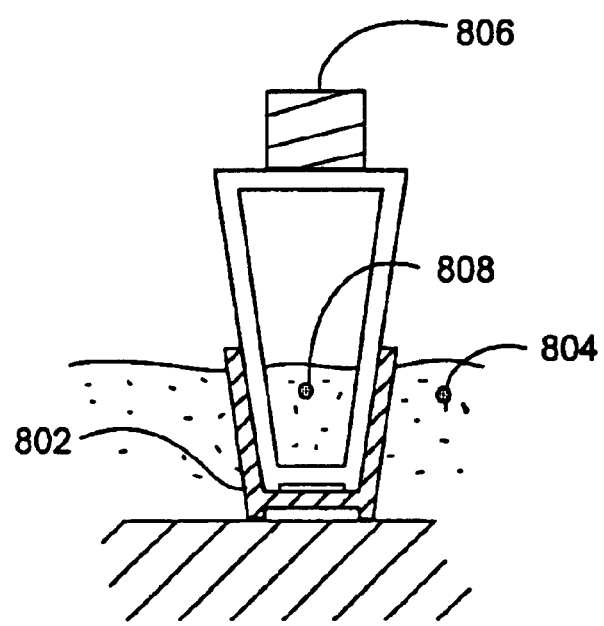

In some embodiments of the present invention, the cryopreservation vial may be removed from frozen outer material and even re-inserted after sampling some of the frozen media comprising the biopharmaceutical product. In such embodiments, the cryopreservation vial may be shaped using the tapered shapes discussed above and/or a cryopreservation vial surface treatment of the outside surfaces that are in contact with frozen cryopreservation media (for example, providing a Teflon coating, applying RF plasma treatment, etc.). The vial can also be inserted into a nest, as illustrated in FIGS. 8A–B. FIG. 8A shows nest 802, which may be made of similar or different material as a cryopreservation vial. FIG. 8B illustrates operation of nest 802. Nest 802 is placed into cryopreservation fluid 804. Cryopreservation vial 806, containing media 808, is placed into nest 802. Nest 802 may remain embedded in frozen cryopreservation fluid 804 while vial 806 may be taken out of it, and later re-inserted into nest 802. The nest's 802 inner shape preferably substantially matches the vial 806 outer dimensions, permitting tight insertion of cryopreservation vial 806 into nest 802 and reducing undesirable insulating air pockets, etc.

In a preferable embodiment, the tips (i.e. end walls) of the nest may be configured to focus the heat flux similar to the heat flux-focusing vial end structures, as described above. Any gap between the nest inner wall and the cryopreservation vial outer wall may be filled with a heat-conducting compound (for example, a silicone grease filled with metal powder). In a preferable embodiment, the dimensions of the vial and its nest may be matched using very close dimensional tolerances, which are close enough that the heat conducting compound may not be needed to obtain substantially uniform heat flux through the vial and nest walls.

Instead of a nest with walls having self-supporting thicknesses, there are other versions of the insert which stays embedded into frozen outer material while vial can be removed and re-inserted: for example, a sealed pocket made of Teflon, polyester or polyamide film packed tightly on vial surface (no air bubbles, nor liquid droplets present between the vial wall and this pocket film wall) inserted into the freezing outer liquid. Since the pocket assumes the vial shape, there will be a cavity in the frozen outer material of the bottom part of the vial, lined with the polymer film (the pocket walls). The vial thus can be removed from that cavity and re-inserted if necessary. The heat flux and temperature distortion around the vial created solely by this polymer film may be insignificant, given the substantial absence of air bubbles or frozen liquid droplets). The film used can also be made of a material that remains flexible at low temperatures applied in this process (down to −80 to −90 C.), such as a silicone elastomer. A single use elastomer is acceptable if there is no re-insertion of the vial back into the frozen outer material.

The dendritic crystal growth similarity outside and inside the vial depends to an extent on temperature gradients in the cryopreservation vial and in the cryopreservation compartment generally. Preferably, temperature gradients are similar within the cryopreservation vial volume and within the space defined as within the cryopreservation compartment but outside the cryopreservation vial. This temperature gradient similarity may be further enhanced by substantially matching the heat conductivity of the cryogenically stable material with the heat conductivity of the frozen cryopreservation fluid and the frozen media. The substantially matching thermal conductivities permit the freezing fronts inside and outside of the cryopreservation vial to move more uniformly together without significant distortions near the cryopreservation vial walls. In an alternative preferable embodiment, the heat conductivity of the cryogenically stable material may be lower than the thermal conductivities of the frozen cryopreservation fluid and the frozen media.

The vial described here will have multiple applications in the cryopreservation processes, and in particular in modeling in small scale the much larger processes. One of the areas where the vial is applied is freezing of biological materials in freezing containers/vessels, which have multiple extended internal heat transfer surfaces. In such freezing systems, there are relationships to be maintained, depending upon the particular application, between the freezing front velocities, interdendritic spacing, temperature gradients, temperature change of the actively (and passively—by heat conduction) cooled surfaces, the distances between the cooled heat transfer surfaces and the product composition (transition points, temperature levels of eutectics and glassy states, solid mass content and solute concentration, etc.).

For example, a control variable of interest in conducting the freezing process in these chambers and in the vial is heat removal from the cryopreservation compartment (i.e. heat flux out of the cryopreservation compartment). In a preferable embodiment, this heat may be controllably and/or variably removed using cooling surfaces. Varying the heat removal may vary the spacing between dendrites formed at the leading edge of a solid front, or within a solid front, that exists within the cryopreservation compartment (which may comprise the volume occupied by one or more cryopreservation vials according to the invention). Varying the interdendritic spacing may be useful for reasons discussed elsewhere in this application. In a preferable embodiment, heat is removed from the cryopreservation compartment at a rate that varies so as to vary an interdendritic spacing at an edge of, or within, a solid front, wherein the solid front is located within the cryopreservation compartment.

Figure 9:
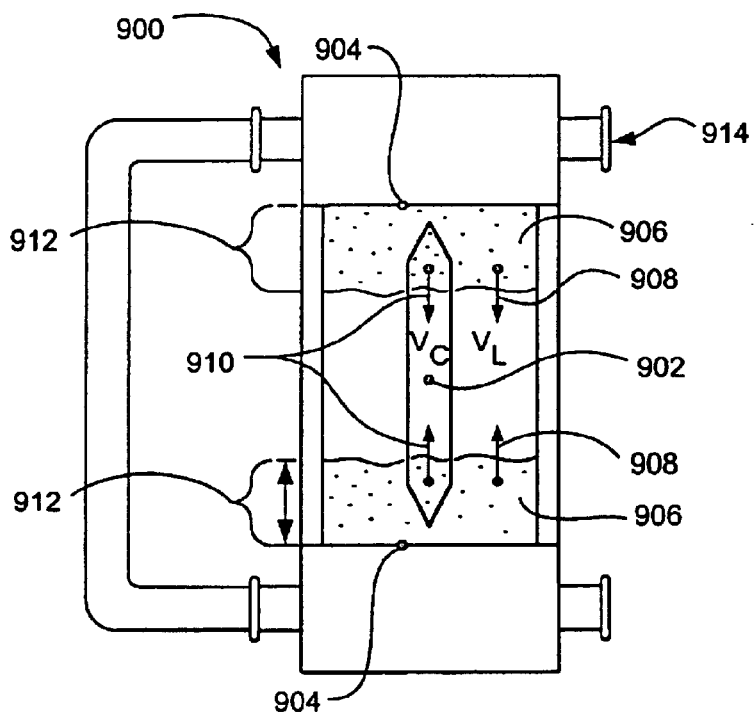
FIG. 9 shows a cross sectional view of a cryopreservation system according to the invention.

In a preferable embodiment of the invention, as shown in FIG. 9, a control system of biopharmaceutical product cryopreservation system 900 may function such that that an increase in thicknesses 912 of solid fronts of frozen media 910 and/or cryopreservation fluid 906 is coupled to an increased heat flux through cooling surfaces 904 (which in turn drives an increased temperature driving force—the difference in temperature between coolants used to cool the cryopreservation compartment steeper temperature gradient) out of the cryopreservation compartment. These changes in the heat flux out of the cryopreservation compartment may be made to maintain a substantially constant temperature driving force across the solid front. In a preferable embodiment, heat is removed at a rate that substantially maintains a temperature driving force within the cryopreservation compartment so as to promote substantially constant freezing solid fronts 906 and/or 910 velocity within the cryopreservation compartment. This may promote an substantially constant freezing front velocity, e.g. provides substantially steady state conditions for undisturbed dendritic ice crystal growth, independently from the distance from the cooled heat transfer surface within the freezing volume. Direction 908 shows the direction of the advancing solid fronts. The flow rate of cooling fluid 914 may be increased and/or the temperature may be decreased to increase the heat flux through cooling surfaces 904.

For example, if the distance between the cooling surfaces is 10 cm and the temperature gradient to be maintained is 10 Deg. C./cm, then the temperature decrease follows the pattern from 0 C. to −50 Deg. C. during the freezing, following the movement of the freezing fronts (e.g. when the fronts are about 3 cm from the cooling surfaces of the cryopreservation compartment, the temperature of those surfaces is about −30 Deg. C. and when the fronts meet the temperature of the cooling surfaces is about −50 Deg. C.

The inventive biopharmaceutical product cryopreservation systems are preferably operated within the temperature and solidification rate ranges that promote uniform ice crystal growth and uniform concentration of solidifying solutes between ice crystals within the cryopreservation vial. This may be accomplished by controlling dendritic ice crystal growth. Controlled dendritic ice crystal growth depends on temperature gradient, directional heat flux and limited undercooling at the dendritic tip. Uniform growth of dendritic ice crystals across bulk volumes of the media comprising the biopharmaceutical product depends upon maintenance of the temperature gradient with the rate of heat removal from the cryopreservation vial (or the biopharmaceutical product cryopreservation system, as the case may be) depending upon the growing thickness of the solidified material.

Such controlled growth ensures similarity of conditions between the dendritic ice crystals where solutes (including biopharmaceutical product contained within the cryopreservation vial) are dehydrated and solidify in a glassy form. The similarity of solidification conditions includes an interdendritic "mushy" zone where solutes becomes concentrated and the temperature within the interdendritic zone decreases until glassy state conditions are reached. Such a glassy state is determined by the glass transition temperature of the media and the water level trapped in the glassy state. In a preferable embodiment, when the dendritic front velocity is maintained to a substantially constant rate, the residence time of solutes (including any biopharmaceutical product) is maintained across the whole cryopreservation vial volume as the dendritic front (and the interdendritic zones associated with it) moves across that volume. The importance of the similarity of the residence time of solutes in the interdendritic zone prior to the solidification into a glassy state is that the solutes (including the biopharmaceutical product) are preferably exposed to similar conditions during the transition from diluted initial liquid product into the glassy state—e.g. the local history of the biopharmaceutical product is similar (time, temperature, concentration, etc.) regardless on location within the cryopreservation vial volume. Similar or substantially similar conditions of dendritic ice crystal growth may be maintained in the cryopreservation compartment as in a full scale (i.e. process-level) cryopreservation system.

Solid front velocities according to the invention may range from about 1 mm/hour to about 800 mm/hour, preferably from about 6 mm/hour to about 140 mm/hour, more preferably from about 12 mm/hour to about 70 mm/hour. Preferably, the temperature gradient within the solid front ranges from about one to about 120 Deg. C./cm, more preferably from about five to about twenty-five Deg. C./cm. Operating temperatures for the inventive biopharmaceutical cryopreservation systems and methods range from about −1 Deg. C. to about −200 Deg. C., more preferably from about −20 Deg. C. to about −200 Deg. C.

An advantage of the inventive cryopreservation compartments is that it minimizes the product volume involved in the research and development work. Using the inventive "scale-down" cryopreservation systems permits rapid testing of the variety of biopharmaceutical products under changing conditions. In a preferable embodiment, the cryopreservation compartment mirror the geometries found in large scale freezing or cryopreservation process vessels.

Figure 10:
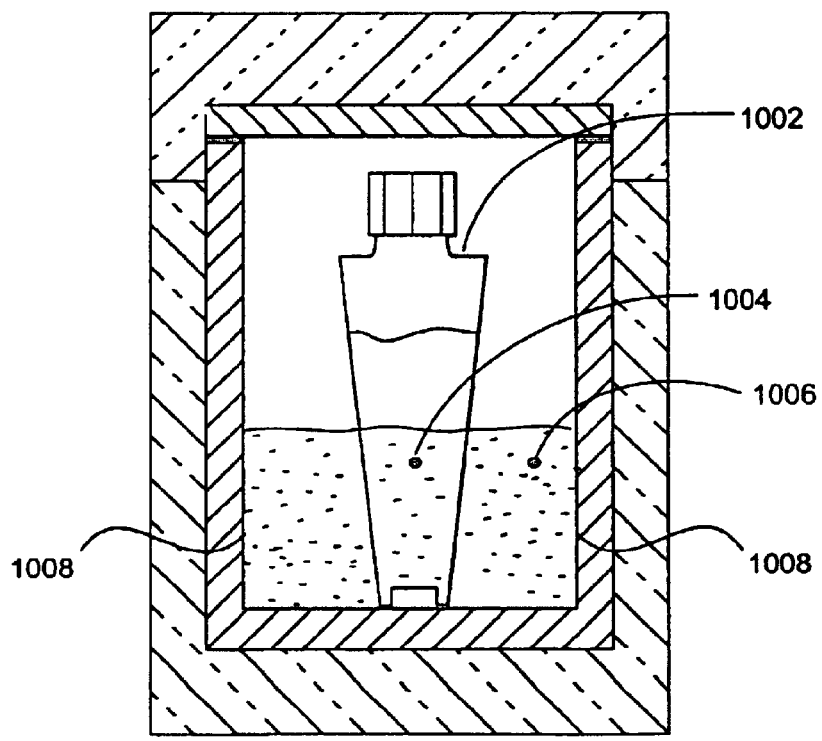
FIG. 10 shows a cross sectional view of a cryopreservation system according to the invention.

As shown in FIG. 10, cryopreservation compartment 1000 may have a form of a simple elongated rectangular chamber with cooling surfaces 1008, which serve to cool and freeze cryopreservation fluid 1006, and media 1004 (contained within cryopreservation vial 1002). In other embodiments, the cryopreservation compartment may have other forms, such as a square or circular/cylindrical shape, or a shape such as those disclosed in U.S. Pat. No. 5,964,100; and U.S. patent application Ser. Nos. 08/895,777; 08/895,782; 08/895,936, and 09/003,283. Such configurations may be selected to retain similarity of the freezing geometry to the large scale process chamber being modeled, similar heat fluxes to the large scale process chamber, similar final operating temperatures, similar temperature control schemes/arrangements (these involve control of the temperature driving force such that it may increase as the solid front advances through the cryopreservation compartment and away from actively cooled surfaces within the cryopreservation compartment. The configurations of vial location in the large scale compartment can ensure the temperature gradient along the frozen product as well as temperature decrease in time at short end(s) of the vial.

The cryopreservation compartment preferably models the freezing and thawing of biopharmaceutical products as they occur in large volume processes. In general, the cryopreservation compartments may have active heat transfer surfaces (cooled by the cooling agent) to generate the outward heat flux (removal of the latent heat of solidification). Cooling of the cryopreservation compartment is preferably accomplished by one or more cooling surfaces. In a preferable embodiment, the one or more cooling surfaces comprise one or more of the internal surfaces of the cryopreservation compartment. Distances between cryopreservation compartment cooling surfaces depend on the applied temperature gradient range. Preferably, the distances between cooling surfaces two or more cooling surfaces spaced apart from one another may vary from about 0.1 mm to about 1500 mm, more preferably from about 1 mm to about 700 mm, most preferably from about 8 mm to about 500 mm.

Cryopreservation fluid formulations typically include numbers of excipients, product stabilization agents and protective compounds. In a preferable embodiment, the cryopreservation fluid is substantially the same as the composition of the media contained within the cryopreservation vial absent the biopharmaceutical product. Such a compositional arrangement promotes similarity of dendritic ice crystal growth within the volume of the cryopreservation vial. This is preferable because similarity of dendritic ice crystal formation inside and outside of the cryopreservation vial leads to improved modeling results applicable to scale up of processes developed using the inventive biopharmaceutical cryopreservation system. Cryopreservation fluids used according to the invention comprise, for example, biological cell cryoprotectants (both penetrating, such as glycerol, dimethylsulfoxide, ethylene glycol, and the like; and non-penetrating, such as hydroxyethyl starch, dextran, polyvinylpyrrolidone and the like), vitrifying agents or components of biopharmaceutical drug formulations (such as surfactants, PEG, carbohydrates, polyols, amino acids or even proteins other than the biopharmaceutical product that is intended to be cryopreserved). The cryopreservation fluid may comprise the same fluids (composition-wise) as found in the media that comprises the biopharmaceutical product, but without the biological component (cell, cell fragments, biopharmaceutical active component) or can be as minimal as water (e.g. distilled, deionized and/or high purity water). Between these two ends a variety of compositions can be applied, such as water and salts (buffers) (like NaCl and water, ammonium sulfate and water, etc.), water and carbohydrates (like sucrose in water, or trehalose in water), water and salts and carbohydrates (like water, NaCl and sucrose), water and PEG, water and detergent/surfactant, and/or water and buffer and carbohydrate and surfactant. Substances used can provide temperature transitions similar to the temperature transitions that occur in the biological product composition (for example, a similarity of glass transition temperatures can be maintained).

Biopharmaceutical products according to the invention comprise any conventional biopharmaceutical or pharmaceutical material. In preferable embodiments, biopharmaceutical products may comprise biological macromolecules such as proteins/enzymes, peptides, DNA, RNA, amino acids, nucleic acids, growth factors, coagulation factors, antibodies, and the like; biological cells or cell fragments/components, including bacteria, fungi, yeast, single cell organisms, mammalian (particularly human) cells, animal cells, plant cells, organelles, cell membranes, inclusion bodies, or pieces of tissue and the like; viral materials; organic or inorganic molecules or ions including stabilizing salts or carbohydrates, antibiotics; or cell growth media. Specific examples include blood and blood products (red and white blood cells, plasma, human serum albumin, etc.), and two or more phase emulsions comprising biological or pharmaceuticals materials.

The cryopreservation vial is preferably located in the external freezing system in such a way that the heat flux from the actively cooled surfaces of that system is approximately parallel to a long axis of the vial. This configuration reduces bulk product supercooling inside the vial and promotes similar freezing conditions inside the vial to the freezing in a large scale cryopreservation system. The freezing fronts move inside and outside the cryopreservation vial with similarity of front velocity and dendritic ice crystal pattern. These conditions promote similar conditions of product freezing (such as similarity of residence time between dendrites prior to solidification, similarity of solutes concentration and temperature distribution among dendrites (in the mushy zone), etc.) outside and inside the vial. The final frozen product preferably will have a similar solute distribution over distance and temperature gradients in both the cryopreservation vial and the large-scale cryopreservation vessel/container.

The vial volume to cryopreservation compartment volume ratio may be small, e.g. to consider freezing in the cryopreservation fluid to be close to an "infinite volume" freezing. However, the depths of the biopharmaceutical product in the vial and the cryopreservation fluid may be preferably maintained substantially similar to reduce effects of thermal conductivity in vial walls (vertical heat flux effects in the vial wall might occur if the outer and inner liquid levels vary significantly).

In an another embodiment, the cryopreservation vial can be matched to the length of the cryopreservation compartment (e.g. the length of the vial approximately equal to the distance between the cooling surfaces of such compartment), or be shorter than that. Shorter vials may be placed in a position where their center matches the location of the center between the actively cooled ends of the large scale compartment. Then the meeting freezing fronts outside the vial and inside the vial are in the centers of both, the vial and the compartment. The vial can also be placed in a position such that its one short end matches the center of the large scale compartment and the other end is close to one of the actively cooled surfaces of the large scale compartment. In this configuration the vial may preferably cover approximately half of the distance between the actively cooled surfaces of the large scale compartment. The last freezing point may still in the cryopreservation compartment center, but in the vial it is one of its ends—such configuration is possible due to any symmetry of the freezing process (when two freezing fronts are approaching each other).

The cryopreservation vial is preferably positioned along the heat flux path, e.g. also substantially in parallel to the directional pattern of dendritic ice crystals (and substantially perpendicularly to the advancing solidification front). The position of the cryopreservation vial in parallel to the dendritic crystals promotes crystal growth similarity inside and outside of the cryopreservation vial. The controlled dendritic ice crystal growth that is useful for optimal cryopreservation of biological material may occur not only outside of the vial in the cryopreservation fluid (freezing front conditions such as parallel heat flux, temperature gradient and front velocity may be maintained there to promote the controlled dendritic crystal growth). The vial interior freezing preferably closely follows the outside freezing pattern, e.g. there is a directional heat flow, there is a similar temperature gradient and the similar front velocity, therefore, the parallel dendritic crystal growth is maintained. The cryopreservation vial may be located in the cryopreservation compartment in such a way that it extends from one active cooling surface to another, permitting freezing modeling across the whole freezing volume—then the freezing fronts will meet inside and outside near the center of the cryopreservation vial. Similarity of the freezing conditions across the whole freezing volume also permits to use shorter cryopreservation vials covering only the part of the external freezing path in the cryopreservation compartment—the product will be frozen as the part of the product of the cryopreservation vial's length would freeze in the cryopreservation compartment.

In a preferable embodiment, multiple cryopreservation vials may be located in the cryopreservation compartment. A preferable configuration will be with the vials' long axis substantially perpendicular to the external freezing front's solid-liquid interfaces. In certain embodiments, the vials may be in a parallel configuration for rectangular compartments, or in "fan-shaped" configurations when the cryopreservation compartment is circular or wedge/section of a circle-shaped, or has a triangular shape, e.g. with appropriate angles among the neighboring vials walls. Such configurations promote approximately parallel growth of ice crystal dendrites inside and outside the vials. The distances between the vials is preferably within the range of about 0.1 to about 200 times the vial width, more preferably within the range of about 1 to about 50 times the vial width.

In certain embodiments, for example wherein the cryopreservation compartment possesses a circular or square shape, the freezing vial shape can comprise bodies in a cross shape, or a multi-arm star shape with nucleating structures coupled to the bodies' distal ends. In such embodiments, the freezing fronts (circular or square) may approach from the all vial ends towards the center. After the ends of vial are embedded, the freezing fronts move together inside and outside the bodies of the cryopreservation vial. The freezing fronts may meet in the center of the vial approaching from all the arms. This freezing pattern may simulate the convergence of freezing fronts in the cylindrical or square cryopreservation container. Angles between the bodies in such cases may range from about five to about ninety degrees, more preferably from about thirty to about ninety degrees. The number of bodies on a cryopreservation vial according to the invention may range from about one to about twelve. In more preferable embodiments, the vials comprise from about two bodies to about eight bodies. In most preferable embodiments, the vials comprise two or six bodies.

It will be apparent to those skilled in the art that various modifications and variations can be made in the circulators, systems and methods of the present invention without departing from the spirit or scope of the invention. Thus, it is intended that the present invention cover the modifications and variations of this invention provided they come within the scope of the appended claims and their equivalents.

What is claimed is:

1. A biopharmaceutical product cryopreservation system, for cryopreserving a biopharmaceutical product, comprising:
    a cryopreservation compartment;
    a cryopreservation fluid located within the cryopreservation compartment; and
    a biopharmaceutical product cryopreservation vial located within the cryopreservation compartment, and
    the biopharmaceutical product cryopreservation vial comprising a body that comprises an oblong cross-section defining proximal and distal ends of the body, and at least one nucleating structure, coupled to at least one distal end of the body, the at least one nucleating structure contacting the cryopreservation fluid, and the body comprising a cryogenically stable material that is compatible with biopharmaceutical products.

2. The biopharmaceutical product cryopreservation system of claim 1, wherein the cryopreservation compartment comprises one or more cooling surfaces.

3. The biopharmaceutical product cryopreservation system of claim 2, wherein the one or more cooling surfaces comprise one or more internal surfaces of the cryopreservation compartment.

4. The biopharmaceutical product cryopreservation system of claim 2, wherein the one or more cooling surfaces comprise two or more cooling surfaces spaced apart from one another.

5. The biopharmaceutical product cryopreservation system of claim 4, wherein a distance between two or more cooling surfaces spaced apart from one another ranges from about 0.1 mm to about 1500 mm.

6. The biopharmaceutical product cryopreservation system of claim 1, wherein the cryopreservation fluid comprises biological cell cryoprotectants, vitrifying agents, components of biopharmaceutical drug formulations, distilled water, buffers, carbohydrates in water, salts and carbohydrates in water, PEG in water, or detergent/surfactant in water.

7. The biopharmaceutical product cryopreservation system of claim 6, wherein the biological cell cryoprotectants comprise penetrating or nonpenetrating cryoprotectants.

8. The biopharmaceutical product cryopreservation system of claim 6, wherein the vitrifying agents or components of biopharmaceutical drug formulations comprise surfactants, PEG, carbohydrates, polyols, amino acids or proteins other than the biopharmaceutical product.

9. The biopharmaceutical product cryopreservation system of claim 1, wherein the biopharmaceutical product cryopreservation system comprises more than one cryopreservation vial.

10. The biopharmaceutical product cryopreservation system of claim 1, wherein the cryopreservation vial comprises media, and the media comprises the biopharmaceutical product.

11. The biopharmaceutical product cryopreservation system of claim 10, wherein the cryopreservation fluid and the media absent the biopharmaceutical product are substantially identical in composition.

12. The biopharmaceutical product cryopreservation system of claim 10, wherein a thermal conductivity and/or a specific heat of the cryopreservation vial walls are substantially similar to those of the media or the cryopreservation fluid.

13. The biopharmaceutical product cryopreservation system of claim 1, wherein the at least one nucleating structure comprises a plurality of nucleating structures.

14. A method of cryopreserving biopharmaceutical products comprising:
    providing a cryopreservation compartment;
    locating a biopharmaceutical product cryopreservation vial within the cryopreservation compartment, wherein the biopharmaceutical product cryopreservation vial comprises a body that comprises an oblong cross-section defining proximal and distal ends of the body, and at least one nucleating structure, coupled to at least one distal end of the body, and the body comprising a cryogenically stable material that is compatible with biopharmaceutical products;
    locating a cryopreservation fluid in a space outside of the cryopreservation vial but within the cryopreservation compartment such that the at least one nucleating structure contacts the cryopreservation fluid; and
    removing heat from the cryopreservation compartment, thereby freezing the cryopreservation fluid.

15. The method of claim 14, wherein the cryopreservation vial comprises media, and the media comprises the biopharmaceutical product.

16. The method of claim 15, wherein the cryopreservation fluid is located so as to contact the at least one nucleating structure.

17. The method of claim 15, wherein the biopharmaceutical product cryopreservation vial is located within the cryopreservation compartment such that a long axis of the oblong cross-section is oriented at an angle to a freezing front defined by freezing of the cryopreservation fluid within the cryopreservation compartment.

18. The method of claim 14, wherein the heat is removed at a rate that substantially maintains a temperature driving force within the cryopreservation compartment so as to promote a substantially constant freezing front velocity within the cryopreservation compartment.

19. The method of claim 14, wherein the heat is removed at a rate that varies so as to vary an interdendritic spacing at an edge of, or within, a solid front, wherein the solid front is located within the cryopreservation compartment.

20. The method of claim 14, wherein the cryopreservation compartment comprises one or more cooling surfaces.

21. The method of claim 20, wherein the one or more cooling surfaces comprise one or more internal surfaces of the cryopreservation compartment.

22. The method of claim 20, wherein the one or more cooling surfaces comprise two or more cooling surfaces spaced apart from one another.

23. The method of claim 22, wherein the distance between two or more cooling surfaces spaced apart from one another ranges from about 0.1 mm to about 1500 mm.

24. The method of claim 14, wherein the cryopreservation fluid comprises biological cell cryoprotectants, vitrifying agents, components of biopharmaceutical drug formulations, distilled water, buffers, carbohydrates in water, salts and carbohydrates in water, PEG in water, or detergent/surfactant in water.

25. The method of claim 24, wherein the biological cell cryoprotectants comprise penetrating or nonpenetrating cryoprotectants.

26. The method of claim 24, wherein the vitrifying agents or components of biopharmaceutical drug formulations comprise surfactants, PEG, carbohydrates, polyols, amino acids or proteins other than the biopharmaceutical product.

27. The method of claim 14, wherein the biopharmaceutical product cryopreservation system comprises more than one cryopreservation vial.

28. The method of claim 14, wherein the cryopreservation vial comprises media, and the media comprises the biopharmaceutical product.

29. The method of claim 28, wherein the cryopreservation fluid and the media are substantially identical in composition.

30. A biopharmaceutical product cryopreservation vial comprising:
   a body that comprises an oblong cross-section taken horizontally between the top and the bottom of the vial and defining proximal and distal ends of the body,
   at least one nucleating structure, coupled to at least one distal end of the body, and
   the body comprising a cryogenically stable material that is compatible with biopharmaceutical products.

31. The biopharmaceutical product cryopreservation vial of claim 30, wherein the cryopreservation vial comprises media, and the media comprises a biopharmaceutical product.

32. The biopharmaceutical product cryopreservation vial of claim 30, wherein the cryogenically stable material that is compatible with biopharmaceutical products comprises a polymer.

33. The biopharmaceutical product cryopreservation vial of claim 30, wherein the polymer comprises polytetrafluoroethylene, polystyrene, polyethylene or polypropylene.

34. The biopharmaceutical product cryopreservation vial of claim 33, wherein the at least one nucleating structure comprises a plurality of nucleating structures.

35. The biopharmaceutical product cryopreservation vial of claim 30, wherein surface treatments have been applied to a surface of the biopharmaceutical product cryopreservation vial.

36. The biopharmaceutical product cryopreservation vial of claim 30, further comprising a vial focusing tip, coupled to the distal end of the body, wherein the vial focusing tip comprises the nucleating structure, and serves to focus heat flux from an oncoming solid front.

37. The biopharmaceutical product cryopreservation vial of claim 36, wherein the vial focusing tip comprises external heat transfer fins.

38. The biopharmaceutical product cryopreservation vial of claim 36, wherein the vial focusing tip comprises internal heat transfer fins.

39. The biopharmaceutical product cryopreservation vial of claim 30, further comprising a vial deflecting tip, coupled to the distal end of the body, wherein the vial deflecting tip comprises the nucleating structure, and serves to deflect oncoming solid front heat flux away from the cryopreservation vial.

40. The biopharmaceutical product cryopreservation vial of claim 30, wherein the nucleating structure comprises one or more points of local proximity.

41. The biopharmaceutical product cryopreservation vial of claim 30, wherein the nucleating structure comprises two or more points of local proximity.

42. The biopharmaceutical product cryopreservation vial of claim 40, wherein the one or more points of proximity comprise wall internal sides of the cryopreservation vial that are formed into extensions located opposite to each other.

43. The biopharmaceutical product cryopreservation vial of claim 42, wherein the internal surface tips of the extensions are spaced apart from about 0.001 mm to about 1 mm.

44. The biopharmaceutical product cryopreservation vial of claim 43, wherein the internal surface tips of the extensions are spaced apart from about 0.04 mm to about 0.5 mm.

45. A biopharmaceutical product cryopreservation system, comprising:
   a cryopreservation compartment adapted to hold cryopreservation fluid; and
   a biopharmaceutical product cryopreservation vial adapted to be located within the cryopreservation compartment, and
   the biopharmaceutical product cryopreservation vial comprising a body that comprises an oblong cross-section defining proximal and distal ends of the body, and at least one nucleating structure, coupled to at least one distal end of the body, the at least one nucleating structure adapted to contact cryopreservation fluid when present within the cryopreservation compartment, and the body comprising a cryogenically stable material that is compatible with biopharmaceutical products.

46. The biopharmaceutical product cryopreservation system of claim 45, wherein the cryopreservation compartment comprises one or more cooling surfaces.

47. The biopharmaceutical product cryopreservation system of claim 46, wherein the one or more cooling surfaces comprise one or more internal surfaces of the cryopreservation compartment.

48. The biopharmaceutical product cryopreservation system of claim 46, wherein the one or more cooling surfaces comprise two or more cooling surfaces spaced apart from one another.

49. The biopharmaceutical product cryopreservation system of claim 48, wherein a distance between two or more cooling surfaces spaced apart from one another ranges from about 0.1 mm to about 1500 mm.

50. The biopharmaceutical product cryopreservation system of claim 45, wherein the biopharmaceutical product cryopreservation system comprises more than one cryopreservation vial.

51. A biopharmaceutical product cryopreservation system, for cryopreserving a biopharmaceutical product, comprising:

a cryopreservation compartment;

a cryopreservation fluid located within the cryopreservation compartment; and a biopharmaceutical product cryopreservation vial located within the cryopreservation compartment, and the biopharmaceutical product cryopreservation vial comprising a body that comprises an oblong cross-section taken horizontally between the top and the bottom of the vial and defining proximal and distal ends of the body, and at least one nucleating structure, coupled to at least one distal end of the body, the at least one nucleating structure contacting the cryopreservation fluid, and the body comprising a cryogenically stable material that is compatible with biopharmaceutical products.

52. A method of cryopreserving biopharmaceutical products comprising:

providing a cryopreservation compartment;

locating a biopharmaceutical product cryopreservation vial within the cryopreservation compartment, wherein the biopharmaceutical product cryopreservation vial comprises a body that comprises an oblong cross-section taken horizontally between the top and the bottom of the vial and defining proximal and distal ends of the body, and at least one nucleating structure, coupled to at least one distal end of the body, and the body comprising a cryogenically stable material that is compatible with biopharmaceutical products;

locating a cryopreservation fluid in a space outside of the cryopreservation vial but within the cryopreservation compartment; and removing heat from the cryopreservation compartment, thereby freezing the cryopreservation fluid.

53. A biopharmaceutical product cryopreservation vial comprising:

a body that comprises an oblong cross-section defining proximal and distal ends of the body, at least two nucleating structures coupled to at least one distal end of the body, and the body comprising a cryogenically stable material that is compatible with biopharmaceutical products.

54. A biopharmaceutical product cryopreservation system, comprising:

a cryopreservation compartment adapted to hold cryopreservation fluid; and a biopharmaceutical product cryopreservation vial adapted to be located within the cryopreservation compartment, and the biopharmaceutical product cryopreservation vial comprising a body that comprises an oblong cross-section taken horizontally between the top and the bottom of the vial and defining proximal and distal ends of the body, and at least one nucleating structure, coupled to at least one distal end of the body, the at least one nucleating structure adapted to contact cryopreservation fluid when present within the cryopreservation compartment, and the body comprising a cryogenically stable material that is compatible with biopharmaceutical products.

* * * * *